(12) United States Patent
Kurahara et al.

(10) Patent No.: US 12,138,251 B2
(45) Date of Patent: Nov. 12, 2024

(54) FIBROSIS DRUG

(71) Applicants: SCIENCE FARM LTD., Kumamoto (JP); LINK GENOMICS, INC., Tokyo (JP)

(72) Inventors: Lin Kurahara, Fukuoka (JP); Hironobu Ihn, Kumamoto (JP); Masami Otsuka, Kumamoto (JP)

(73) Assignees: SCIENCE FARM LTD., Kumamoto (JP); LINK GENOMICS, INC., Tokyo (JP)

(*) Notice: Subject to any disclaimer, the term of this patent is extended or adjusted under 35 U.S.C. 154(b) by 254 days.

(21) Appl. No.: 17/426,898

(22) PCT Filed: Jan. 30, 2020

(86) PCT No.: PCT/JP2020/003522
§ 371 (c)(1),
(2) Date: Jul. 29, 2021

(87) PCT Pub. No.: WO2020/158890
PCT Pub. Date: Aug. 6, 2020

(65) Prior Publication Data
US 2022/0096448 A1 Mar. 31, 2022

(30) Foreign Application Priority Data

Jan. 31, 2019 (JP) ................ 2019-015226

(51) Int. Cl.
*A61K 31/44* (2006.01)
*A61P 1/12* (2006.01)

(52) U.S. Cl.
CPC .............. *A61K 31/44* (2013.01); *A61P 1/12* (2018.01)

(58) Field of Classification Search
CPC .................................................. A61K 31/44
See application file for complete search history.

(56) References Cited

PUBLICATIONS

Bettenworth et al. (Fibrogenesis & Tissue Repair, 2014, 7:5, p. 1-16).*
Luong et al. (Abstracts from the 41st Annual Meeting/Journal of Dermatological Science 86, 2017, e1-e95).*
ISR for PCT/JP2020/003522, dated Feb. 25, 2020.
Naito et al., "Clinical Studies of Molecular Targeted Therapies for Inflammatory Bowel Disease", Journal of Kyoto Prefectural University of Medicine, 2014, 123(4):233-245 (w/ partial translation).
Hai et al., "Counteracting effect of TRPC1-associated $Ca^{2+}$ influx on TNF-α-induced COX-2-dependent prostaglandin $E_2$ production in human colonic myofibroblasts", Am J Physiol Gastrointest Liver Physiol, 2011, 301:G356-G367.
Luong et al., "Blockade of TGF-β/Smad signaling by the small compound HPH-15 ameliorates experimental skin fibrosis", Arthritis Research & Therapy, 2018, 20(46):1-13.
Ihn, "Autocrine TGF-ß signaling in the pathogenesis of systemic sclerosis", Journal of Dermatological Science, 2008, 49: 103-113.
Rieder et al., "Intestinal fibrosis in inflammatory bowel disease—Current knowledge and future perspectives", Journal of Crohn's and Colitis, 2008, 2:279-290.
Definition of "fibrosis", Experimental Medicine Online, https://www.yodosha.co.jp/jikkenigaku/keyword/2007.html (w/ translation) (printed on Jun. 2, 2021) [submitted with Aug. 19, 2021 IDS].
Fibrotic disease—Immunology Frontier Research Center, Osaka University, http://www.ifrec.osaka-u.ac.jp/jpn/research/upload_img/commentary20161222_j.pdf (2016) (w/ partial translation) [submitted with Aug. 19, 2021 IDS].
Kurahara, "Novel therapeutic approaches of intestinal stenosis focused on myofibroblasts", Grants-in-Aid for Scientific Research (Subsidies for Grants-in-Aid for Scientific Research) Final Research Report, Young Scientists (B), Project No. 22790677 (2013) (w/ partial translation) [submitted with Aug. 19, 2021 IDS].
"Systemic Sclerosis (designated intractable disease 51)", Japan Intractable Diseases Information Center, https://www.nanbyou.or.jp/entry/4027 (w/ partial translation) (printed on Jun. 2, 2021) [submitted with Aug. 19, 2021 IDS].

* cited by examiner

*Primary Examiner* — Bong-Sook Baek
(74) *Attorney, Agent, or Firm* — Greenblum & Bernstein, P.L.C.

(57) ABSTRACT

The present invention provides a pharmaceutical composition for preventing and/or treating a disease characterized by fibrosis of a cell or a tissue, the pharmaceutical composition comprising a compound represented by formula 1 or a salt thereof, and a pharmaceutically acceptable carrier.

3 Claims, 4 Drawing Sheets

FIBROSIS DRUG

TECHNICAL FIELD

The present invention relates to a drug for treating fibrotic diseases, particularly inflammatory bowel diseases and systemic sclerosis.

BACKGROUND ART

"Fibrosis" is a phenomenon in which connective tissue in tissues abnormally proliferates, which is caused by an excessive deposition of extracellular matrix such as collagen produced by fibroblasts, and observed in diseases such as hepatic cirrhosis, scleroderma, and keloid; as for its molecular mechanism, an abnormality of intracellular signals, notably TGF-β, has been revealed (non-patent document 1).

"Fibrotic disease" is a disease in which when a biogenic organ such as lungs or a liver is once damaged and the process of repairing erroneously leads to the accumulation of collagenous fibers such as type I collagen, the organ loses its elasticity to become hardened and cannot normally function, which is a disease that can occur in important organs such as lungs, a heart, a liver, kidneys, or skin (non-patent document 2).

As fibrotic disease, which causes abnormal deposition of the extracellular matrix such as collagen produced by fibroblasts, fibrotic disease of various organs such as fibrotic disease of the lung, liver fibrotic, renal fibrosis, fibrotic disease of the digestive organ, and skin fibrosis is known. Increased accumulation of collagen through TGF-β-Smad signaling is common to fibrotic disease.

Inflammatory bowel diseases such as Crohn's disease and ulcerative colitis are a disease group in which chronic inflammation and/or ulceration occur in the mucosa of the large intestine and/or the small intestine. Overproduction of proinflammatory cytokine TNF-α is considered as a main mechanism of intestinal inflammation, fibroblasts existing in the stroma below the intestinal mucosal epithelium change in trait to become myofibroblasts, and PGE2 is produced by the expression of COX-2 induced through the activation of transcription factor NF-κB. Treatment with anti-TNF-α antibodies has been successful. On the other hand, in inflammatory bowel diseases, intestinal stenosis due to fibrosis caused by increased expression of a collagen gene via TGF-β-Smad signaling has been a major problem; currently, there is no drug therapy for this, and the main therapy is surgical resection or endoscopic balloon dilation (non-patent document 3, non-patent document 4, and non-patent document 5).

Systemic sclerosis (SSc) is a chronic disease characterized by a change in which the skin and/or an internal organ become hardened (referred to as induration). However, it should be noted that the degree and progress of the induration vary from patient to patient. From this point of view, two main categories of systemic sclerosis are widely used internationally. That is, systemic sclerosis is classified into "diffuse cutaneous systemic sclerosis," which shows typical symptoms, and "limited cutaneous systemic sclerosis," which is a relatively mild form. The former often progresses within 5 to 6 years from the onset, while the latter, which is the mild form, progresses little or slowly. Note that "localized scleroderma" is a completely different disease in which the induration occurs only in the skin, and is completely different from the aforementioned "limited cutaneous systemic sclerosis." The etiology of systemic sclerosis is complex and the pathology thereof has not been fully elucidated. However, previous studies have revealed its deep association with the following three abnormalities: (1) abnormal immunity; (2) fibrosis; and (3) vascular disorder. However, the interrelationship therebetween and the etiology remain unclear (non-patent document 6 and non-patent document 7).

PRIOR ART DOCUMENTS

Non-patent Documents

Non-patent Document 1: Experimental Medicine Online (<https://www.yodosha.co.jp/jikkenigaku/keyword/2007.html>)

Non-patent Document 2: Fibrotic disease Immunology Frontier Research Center, Osaka University <http://www.ifrec.osaka-u.ac.jp/jpn/research/upload_img/commentary20161222_j.pdf>

Non-patent Document 3: Yuji Naito, Kazuhiko Uchiyama, Tomoshisa Takagi, Molecular Targeted Therapies for Inflammatory Bowel Disease (IBD), Journal of Kyoto Prefectural University of Medicine, 123 (4), 233-245, 2014.

Non-patent Document 4: Lin Kurahara, Grants-in-Aid for Scientific Research (Subsidies for Grants-in-Aid for Scientific Research) Final Research Report, Novel therapeutic approaches of intestinal stenosis focused on myofibroblasts, Young Scientists (B), Project No. 22790677

Non-patent Document 5: Lin Hai, Yasuhiro Kawarabayashi, Yuko Imai, Akira Honda, and Ryuji Inoue, Counteracting effect of TRPC1-associated Ca2+influx on TNF-α-induced COX-2-dependent prostaglandin E2 production in human colonic Myofibroblasts, Am J Physiol Gastrointest Liver Physiol 301: G356-G367, 2011.

Non-patent Document 6: Japan Intractable Diseases Information Center, Systemic Sclerosis (designated intractable disease 51) (<http://www.nanbyou.or.jp/entry/4027>)

Non-patent Document 7: Hironobu Ihn, Autocrine TGF-β signaling in the pathogenesis of systemic sclerosis, Journal of Dermatological Science (2008) 49, 103-113.

SUMMARY OF THE INVENTION

Object to be Solved by the Invention

Therefore, there has been a need for medicaments effective in treating diseases due to fibrosis of a cell.

In the prevention and/or treatment of the above-described fibrotic disease or the like, suppression of the collagen production via TGF-β-Smad signaling can be a strong strategy.

Means to Solve the Object

As a result of intensive studies, the present inventors have synthesized various compounds having a basic skeleton with pyridine having a side chain at its 2- and 6-positions, and found a compound represented by formula (1) detailed below (also referred to as "HPH-15" in the present specification) as a compound having a suppressing activity on the collagen production via TGF-β-Smad signaling.

Accordingly, the present invention includes the following:
[1] A pharmaceutical composition for treating a disease characterized by fibrosis of a cell or a tissue due to an excessive deposition of collagen, the pharmaceutical composition comprising: a compound represented by formula 1:

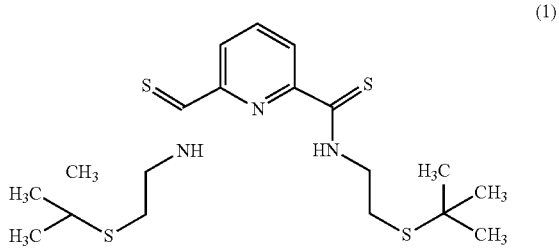

(1)

or a salt thereof; and a pharmaceutically acceptable carrier, wherein the disease is selected from the group consisting of

[2] A method for producing a medicament for treating a disease characterized by fibrosis of a cell or a tissue due to an excessive deposition of collagen, the method comprising a step of mixing a compound represented by formula 1:

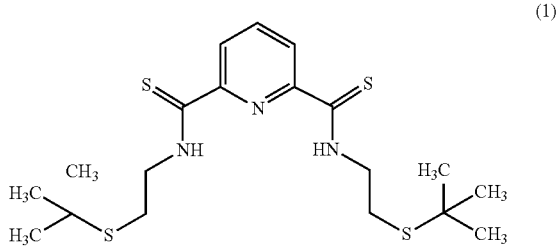

(1)

or a salt thereof together with a pharmaceutically acceptable carrier to formulate the medicament, wherein the disease is selected from the group consisting of a fibrotic disease, an inflammatory bowel disease, and a systemic sclerosis.

[3] Use of a compound represented by formula 1:

(1)

or a salt thereof in production of a medicament for treating a disease characterized by fibrosis of a cell or a tissue due to an excessive deposition of collagen, wherein the disease is selected from the group consisting of a fibrotic disease, an inflammatory bowel disease, and a systemic sclerosis.

Effect of the Invention

The compound of the present invention has a suppressing activity on fibrosis of a cell due to collagen production.

The pharmaceutical composition of the present invention can suppress a symptom of a disease characterized by fibrosis of a cell due to increased expression of a collagen gene or increased production of collagen.

MODE OF CARRYING OUT THE INVENTION

1. Definitions of Terms

Figure 1:
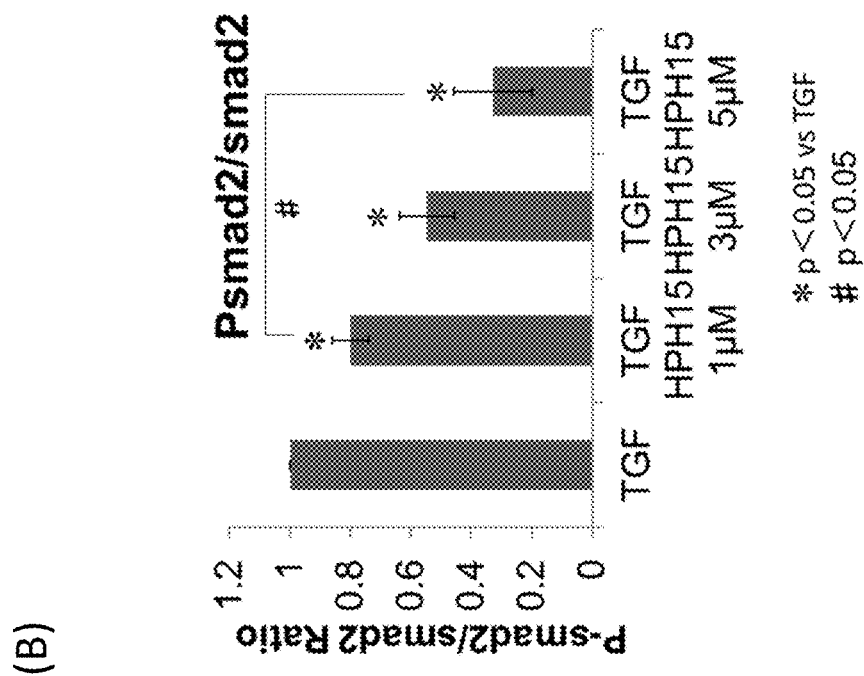
FIG. 1 shows Smad phosphorylation, which increases by stimulation of InMyoFib cells with TGF-β1, changing according to HPH-15.
Figure 1:
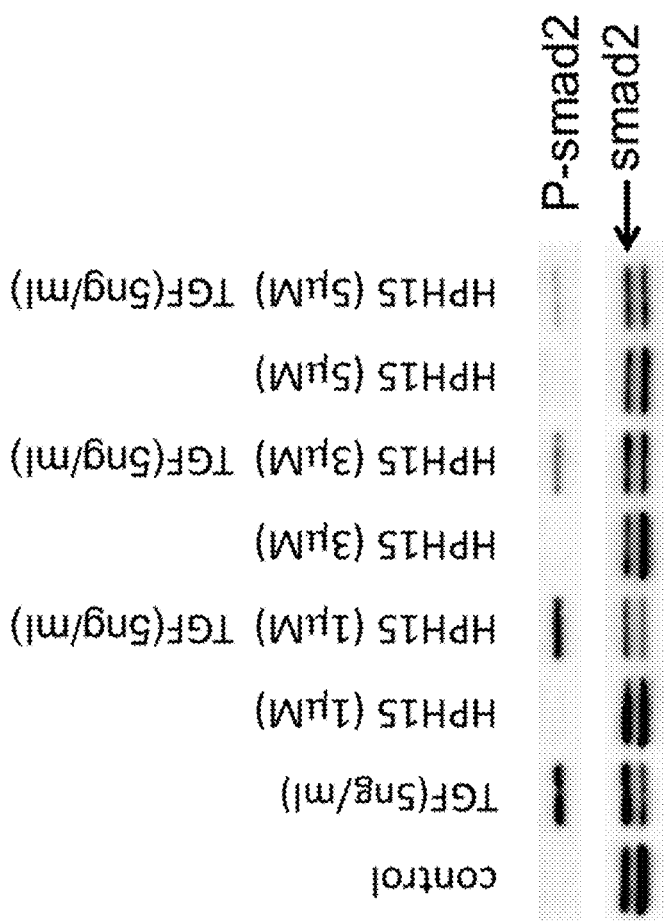

The term "collagen" as used in the present specification, unless otherwise specified, is used to refer to a collagen protein, and the term "collagen gene" is used to refer to a gene encoding a collagen protein. Collagen is one of proteins mainly constituting dermis, ligaments, tendons, bones, cartilages, etc. in vertebrates, and is the main component of the extracellular matrix in multicellular animals (Wikipedia).

In the present specification, terms such as "an overaccumulation of collagen," "an increased accumulation of collagen," "an excessive deposition of collagen," "an abnormal deposition of collagen," and "an increased production of collagen" are used as synonyms. In addition, in the present specification, an expression such as "an increased expression of a collagen gene" for a collagen gene is used to refer to a phenomenon similar to the "increased production of collagen."

In the present specification, terms such as "fibrotic disease," "inflammatory bowel disease(s)," and "(systemic) sclerosis" are used in the meanings commonly used in the art.

The term "salt" as used in the present specification is used in the meaning commonly used in the art. The "salt," in a broad sense, refers to a compound in which a negatively charged ion (an anion) derived from an acid is ionically bonded with a positively charged ion (a cation) derived from a base, and in a narrow sense, refers to an equivalent mixture of an Arrhenius acid and an Arrhenius base. The "salt" can be generated not only by a neutralization reaction between an acid and a base but also by a reaction between an acid and a basic oxide or a single metal, a reaction between a base and an acidic oxide or a single nonmetal, a reaction between an acidic oxide and a basic oxide, or a reaction between a single nonmetal and a metal (Wikipedia).

Examples of a salt that the compound of the present invention forms with a base include, but are not limited to, a salt with an inorganic base of sodium, potassium, magnesium, calcium, or aluminum; and a salt with an organic base such as methylamine, ethylamine, and ethanolamine. In addition, the salt may also be an acid addition salt, which includes, for example, but are not limited to, an acid addition salt with a mineral acid such as hydrochloric acid, hydrobromic acid, hydroiodic acid, sulfuric acid, nitric acid, or phosphoric acid; and an acid addition salt with an organic acid such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, or ethanesulfonic acid. These salts may be conventional ones that are pharmacologically acceptable.

The method for producing a salt of the compound according to the present invention can be performed by appropriately combining methods commonly used in the field of organic synthetic chemistry. A specific example of the method includes neutralization titration of a free solution of the compound according to the present invention with an alkali solution or an acid solution.

2. Pharmaceutical Composition Containing a Compound Represented by Formula (1)

The present invention provides a pharmaceutical composition for treating a disease characterized by fibrosis of a cell or a tissue due to an excessive deposition of collagen, the pharmaceutical composition containing: a compound represented by the formula:

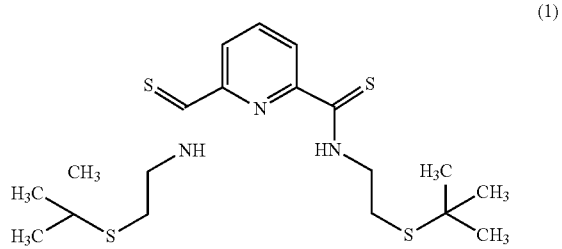

(1)

or a salt thereof; and a pharmaceutically acceptable carrier.

The compound represented by formula (1) of the present invention can be used as a medicament for treating a disease characterized by fibrosis of a cell or a tissue due to an excessive deposition of collagen. The test subject can be a human or an animal (e.g., a non-human mammal).

The compound of the present invention, as it is or upon being formulated together with a pharmaceutically acceptable carrier or the like into a medicament, can be administered to a human or an animal for the treatment of various diseases.

In addition, the compound of the present invention can be used for producing a medicament for treating various diseases characterized by a disease characterized by fibrosis of a cell or a tissue due to an excessive deposition of collagen.

The compound of the present invention or a pharmaceutical composition including the same may be provided as one component included in a medical (e.g., therapeutic or prophylactic) kit. The kit may include, in addition to the compound or the pharmaceutical composition, instructions describing how to apply, how much to apply, etc.

Representative examples of the above "disease characterized by fibrosis of a cell or a tissue due to an excessive deposition of collagen" include, but are not limited to, fibrotic disease of various organs including fibrotic disease of the lung, liver fibrosis, kidney fibrosis, fibrotic disease of the digestive organ, and skin fibrosis, inflammatory bowel diseases including Crohn's disease and ulcerative colitis, and systemic sclerosis.

In the present specification, the terms "pharmaceutically acceptable" or "pharmacologically acceptable" are used to refer to such a compound, material, composition, and/or dosage form that are free from excessive toxicity, stimulation, an allergic reaction, or other problems or a complication, are commensurate with a reasonable benefit/risk ratio, and are within the confines of a proper medical decision that they are suitable for use in contact with human and animal tissues.

Examples of the "pharmaceutically (pharmacologically) acceptable carrier" as used in the present specification include any solvent, dispersion medium, coating, surfactant, antioxidant, preservative (e.g., antibacterial agent, antifungal agent), isotonic agent, absorption delaying agent, salt, preservative, medicament, drug stabilizer, gel, binder, additive, disintegrant, lubricant, sweetener, flavoring agent, dye, and/or material therefor and a combination thereof that are known to those skilled in the art.

The "treatment" or "treat(ing)" as used in the present specification includes (i) preventing a pathological condition from occurring (e.g., prophylaxis), (ii) inhibiting the pathological condition or arresting the development thereof, and (iii) reducing, remitting, or completely recovering from the pathological condition, and/or reducing, remitting, or completely recovering from a symptom associated with the pathological condition.

The compound of the present invention can be used as it is or as a pharmacologically acceptable salt thereof. Examples of the pharmacologically acceptable salt include an alkali metal salt such as sodium salt or potassium salt, or an ammonium salt.

When the compound of the present invention or a pharmacologically acceptable salt thereof is administered as a pharmaceutical composition, for example, the active ingredient that is the compound or the pharmaceutically acceptable salt thereof can be formulated alone or in combination with a conventional excipient into an appropriate dosage form such as a capsule, a tablet, or an injection for use in oral or parenteral administration. For example, the capsule can be prepared by mixing the compound of the present invention or a salt thereof with an excipient such as lactose, starch, or a derivative thereof, or a cellulose derivative, and filling the mixture into a gelatin capsule.

The tablet can be prepared by adding a binder such as sodium carboxymethyl cellulose, alginic acid, or gum arabic and water in addition to the above-described excipient, kneading the mixture, optionally granulating the mixture, then further adding a lubricant such as talc or stearic acid, and using a conventional compression tableting machine.

In the parenteral administration by injection, the compound of the present invention or a salt thereof is dissolved together with a solubilizing agent in sterile distilled water or sterile physiological saline, and encapsulated in an ampule to give an injectable formulation. If necessary, a stabilizer, a buffer substance, or the like may be contained. These formulations for the parenteral administration can be administered intravenously or by intravenous drip.

The dosage of the compound of the present invention will vary depending on various factors such as the symptom, severity, age, or presence or absence of a complication of a patient to be treated. In addition, the dosage will also vary depending on the administration route, dosage form, administration frequency, or the like; however, typically, in the case of oral administration, the active ingredient can be appropriately selected and administered usually within the range of from 0.1 to 1000 mg/day/human, preferably from 1 to 500 mg/day/human, and in the case of parenteral administration, within the range of about 1/100 to 1/2 of the dosage for the oral administration.

The present invention will be described in more detail with reference to the following Examples. These Examples are exemplary and do not limit the scope of the invention in any manner.

The method for synthesis of the compound of the present invention specifically described in the following Examples follows the method described in Hosono et al., Bioorganic Medicinal Chemistry Letters, vol 18, page 371-374, 2008, the whole of which is incorporated in the present specification for reference.

EXAMPLES

Example 1

Immunoblot Study of the Effect of HPH-15 on Human Colon Myofibroblast Cell Line InMyoFib An InMyoFib human colon myofibroblast cell line, which reproduces an inflammatory bowel disease, was used. The culture condition was as follows: culture medium SmBM with 5% fetal bovine serum (FBS), antibiotics, and growth factors (insulin, hFGF-B, hEGF, FBS, and gentamicin/amphotericin-B). Cells at 10 to 17 passages were used. The cells were stimulated with TGF-$\beta$1 (5 ng/ml) and HPH-15 (1% serum FBS concentration) for 24 hours, and observed by immunoblot for collagen involved in fibrosis and phosphorylated Smad.
[Results]

As shown in FIG. 1, the amount of phosphorylated Smad (P-Smad), which increases by stimulation of InMyoFib cells with TGF-$\beta$1, was reduced by the HPH-15 treatment in a dose-dependent manner.

Figure 2:
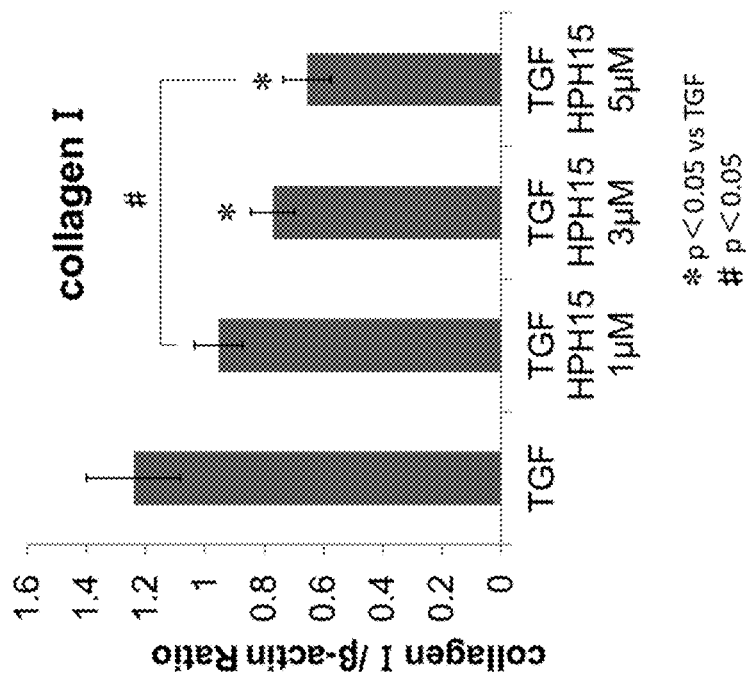
FIG. 2 shows the amount of collagen I, which increases by stimulation of InMyoFib cells with TGF-β1, changing according to HPH-15.
Figure 2:
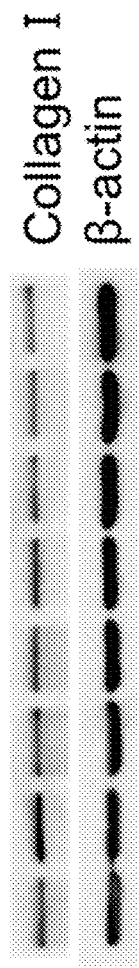

As shown in FIG. 2, the amount of collagen I, which increases by stimulation of InMyoFib cells with TGF-$\beta$1, was reduced by the HPH-15 treatment in a dose-dependent manner.

From FIG. 1 and FIG. 2, it was shown that HPH-15 inhibited the collagen production via TGF-$\beta$-Smad signaling in the InMyoFib cells.

Example 2

Immunoblot Study of the Effect of HPH-15 on a Human Dermal Fibroblast Cell Line

Human dermal fibroblasts are incubated with 2 ng/mL TGF-$\beta$ for 24 hours to turn into scleroderma, and incubated for 48 hours with addition of 5 $\mu$M or 10 $\mu$M HPH-15. Collagen was observed by immunoblot.
[Results]

Figure 3:
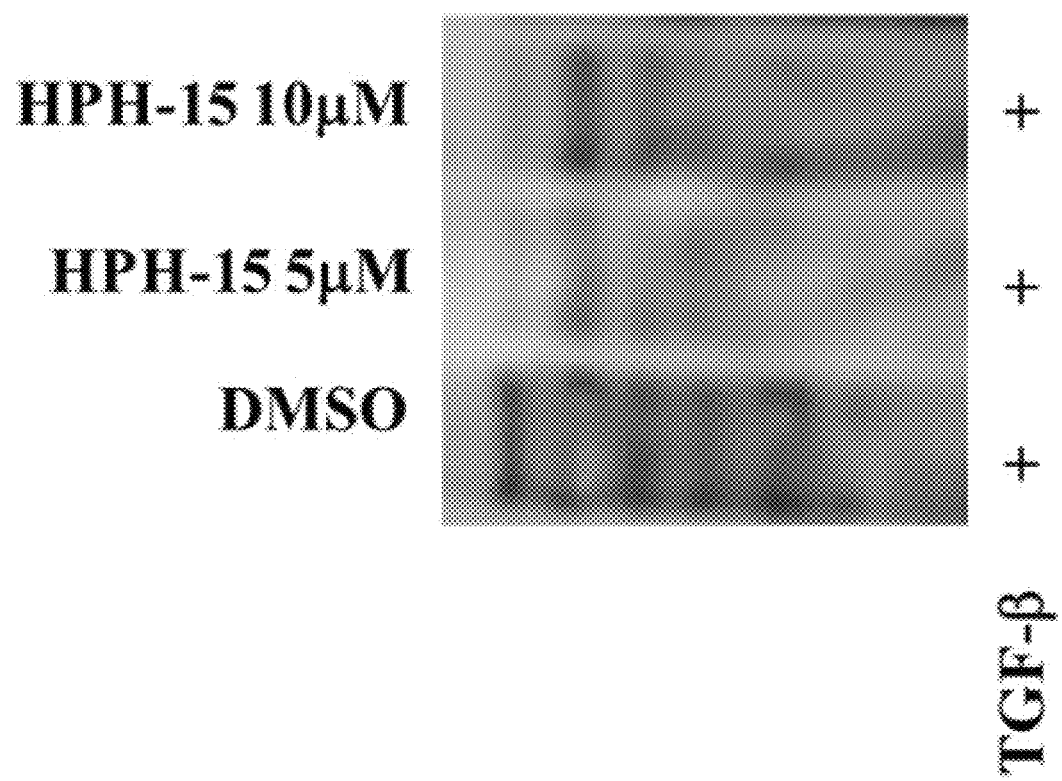
FIG. 3 shows the amount of collagen I, which increases by stimulation of a human dermal fibroblast cell line with TGF-β1, changing according to HPH-15.

As shown in FIG. 3, the expression of collagen was suppressed with 5 $\mu$M or 10 $\mu$M HPH-15.

Example 3

Experiment on an Inflammatory Bowel Disease Mouse Model Using HPH-15

The therapeutic effect of HPH-15 on the inflammatory bowel disease was examined using an inflammatory bowel disease mouse model.

Example 4

Experiment on a Scleroderma Mouse Model Using HPH-15

The therapeutic effect of HPH-15 on scleroderma was examined using a scleroderma mouse model.

Specifically, in order to study the dose-dependent effect of HPH-15, the inhibitory effect on skin induration with HPH-15 at each of doses of 50, 100, 200, and 300 mg/kg/day was studied in a bleomycin (BLM)-induced scleroderma mouse model. For the bleomycin (BLM)-induced scleroderma mouse model in this study, a treatment model was used in which bleomycin was administered for 2 weeks and then HPH-15 (dissolved in olive oil) was orally administered in combination therewith for 4 weeks.

Figure 4:
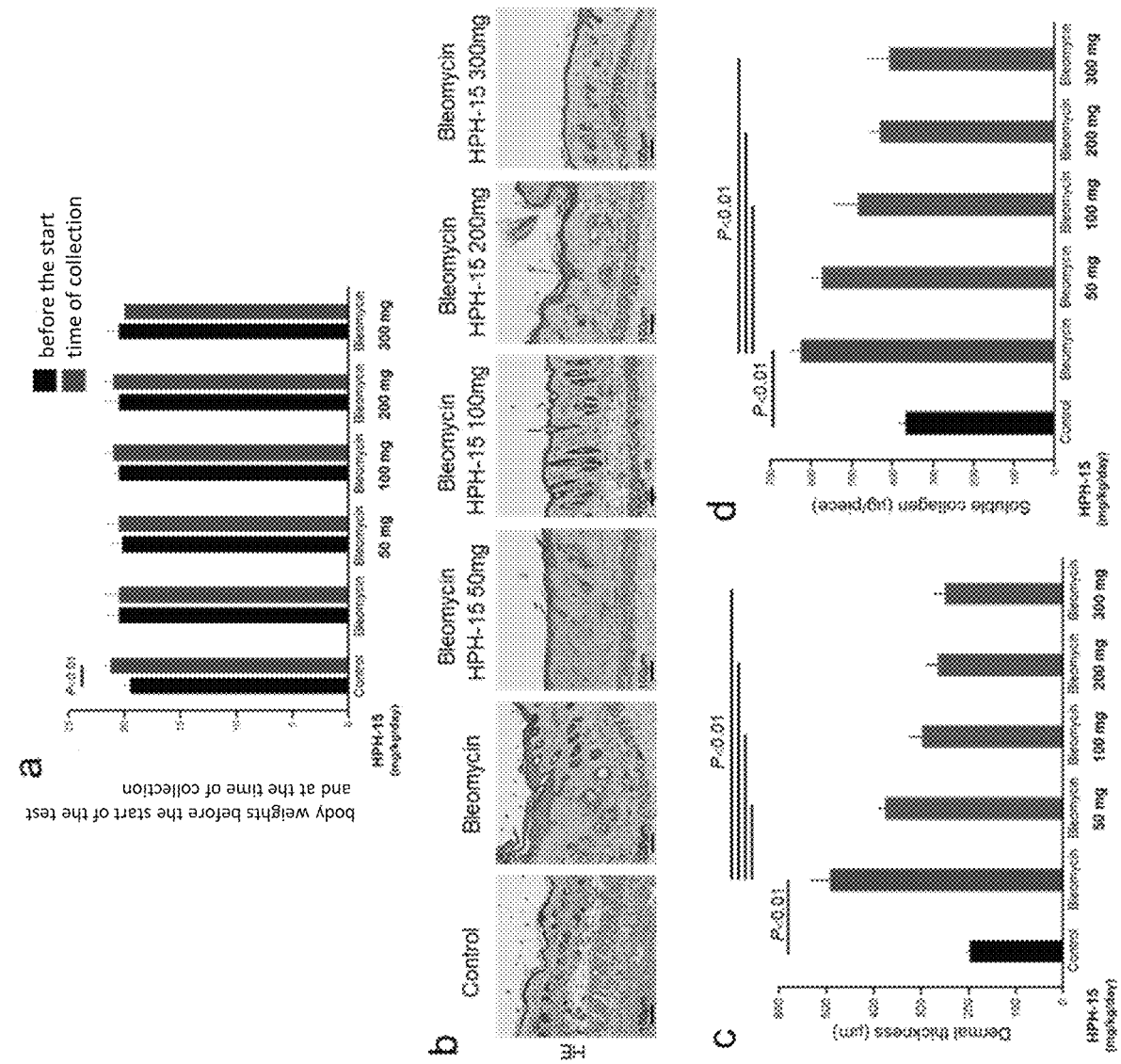
FIG. 4 shows the results of examining the dose-dependent inhibitory effect of HPH-15 on skin induration in a bleomycin (BLM)-induced scleroderma mouse model. a: The results of measuring and comparing body weights of mice before the start of the test and at the time of tissue collection (6 weeks later) for a control, a bleomycin-only group, and each HPH-15-dose group (50, 100, 200, 300 mg/kg/day) are shown. b: A representative stained image of each group obtained by HE staining of mouse skin tissue collected with a scalpel and a knife is shown. c: A graph showing the result of measuring and comparing the distance between the skin dermis boundary and the subcutaneous fatty tissue using the HE-stained image for each group. d: A graph showing a comparison of the amount of collagen in the skin tissue for each group.

At the time of collecting the skin (6 weeks after the start of the test), no significant decrease in body weight was observed at each dose of HPH-15 as compared with that before the start of the test, and the systemic condition of the mice was kept well (FIG. 4a). HE staining was performed on the collected mouse skin tissues, and the skin thicknesses were compared. As a result, the dermal thickness increased by bleomycin was significantly reduced at an HPH-15 dose of 50 mg/kg/day or more (FIGS. 4b, c). In addition, as a result of measuring collagen from the skin tissue, the amount of dermal collagen increased by bleomycin was significantly reduced at an HPH-15 dose of 100 mg/kg/day or more (FIG. 4d).

<Experimental Protocol>

The dose-dependent effect of HPH-15 in the treatment protocol for the bleomycin (BLM)-induced scleroderma mouse model was studied. An eight-to-ten-week-old female C57BL/6 mouse was injected subcutaneously with 150 $\mu$l of bleomycin (dissolved in physiological saline at 1 mg/ml) or with 150 $\mu$l of physiological saline as a control on the shaved back once a day for 6 weeks on alternate days. From 2 weeks after the start of bleomycin injection, HPH-15 dissolved in olive oil was orally administered in combination therewith once a day at doses of 50, 100, 200, and 300 mg/kg/day (the dosage of olive oil was 200 $\mu$l/day).

a. For each group, the body weights of the mice before the start of the test and at the time of the tissue collection (6 weeks later) were measured and compared. A Student's t-test was used for statistics. Four mice are used for each group. A gain in body weight at the time of the collection was observed in the control group. No change in body weight was observed in the bleomycin-only group and the HPH-15-dose groups (FIG. 4a).

b. Mouse skin tissue for HE staining was collected with a scalpel and a knife. The skin tissue was fixed with 4% paraformaldehyde, and HE-stained slides were prepared from the paraffin block. A representative stained image of each group was shown (FIG. 4b).

c. For the dermal thickness, the distance between the epidermis-dermis boundary and the subcutaneous fatty tissue was measured using HE staining. For statistics, a parametric multiple comparison test by the Tukey- Kramer method was performed. Four mice were used for each group. The dermal thickness increased by bleomycin was significantly reduced at an HPH-15 dose of 50 mg/kg/day or more (FIG. 4c).

d. In order to compare the amounts of collagen in the skin tissues, the skins were collected using a 4 mm Derma punch centering on the bleomycin-injected site on the back skin of the mice. For the measurement of the amount of collagen, Sircol Soluble Collagen Assay Kit (#S1000, Funakoshi Co., Ltd.) was used. The amount (μg) of collagen in the skin tissue was graphed using four mice for each group. For statistics, the Tukey-Kramer method was used. The amount of collagen in the skin tissue is increased by the administration of bleomycin as compared with the control group. The amount of collagen in the skin was significantly reduced at an HPH-15 dose of 100 mg/kg/day or more as compared with the bleomycin-only-administered group (FIG. 4d).

While the present invention has been specifically described above with reference to the Examples, the technical scope of the present invention is not limited to these Examples, and various variations are possible within the technical scope of the invention as defined by the appended claims and equivalents thereof based on the teachings of the present specification and the drawings as well as the common technical knowledge in the art at the time of filing of the present application, and these variations are also included in the technical scope of the present invention.

INDUSTRIAL APPLICABILITY

The compound of the present invention can be used in a pharmaceutical composition or kit for treating various diseases characterized by fibrosis of a cell due to collagen production, or a method for treating the diseases using the pharmaceutical composition or kit. The compound of the present invention or a salt thereof is useful as a medicament for inhibiting cellular transformation.

The invention claimed is:

1. A method for treating inflammatory bowel disease, comprising administering to a subject in need thereof a compound represented by formula 1:

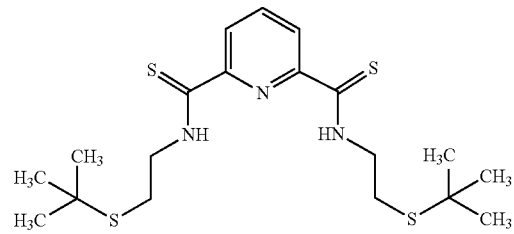

or a salt thereof.

2. The method of claim 1, wherein the inflammatory bowel disease is Crohn's disease or ulcerative colitis.

3. The method of claim 1, wherein the inflammatory bowel disease is Crohn's disease.

* * * * *